US00PP12955P2

(12) United States Plant Patent
Kramer

(10) Patent No.: US PP12,955 P2
(45) Date of Patent: Sep. 17, 2002

(54) GERANIUM PLANT NAMED 'BLOGOLD'

(75) Inventor: Hans Kramer, Ede (NL)

(73) Assignee: Blooms of Bressingham, Ltd., Norfolk (GB)

( * ) Notice: Subject to any disclaimer, the term of this patent is extended or adjusted under 35 U.S.C. 154(b) by 0 days.

(21) Appl. No.: 09/227,882

(22) Filed: Jan. 11, 1999

(51) Int. Cl.[7] ..... A01H 5/00
(52) U.S. Cl. ..... Plt./324
(58) Field of Search ..... Plt./324

(56) References Cited

FOREIGN PATENT DOCUMENTS

EP 1996/325 11/1996

OTHER PUBLICATIONS

Blooms Wholesale Plant Promotions 2000 Catalogue (2000).

European Union Community Plant Variety Gazette No. Jan. 1997 (1997).

European Union Community Plant Variety Gazette No. Mar. 2000 (2000).

*Primary Examiner*—Bruce R. Campell
*Assistant Examiner*—Michelle Kizilkaya
(74) *Attorney, Agent, or Firm*—Foley & Lardner

(57) ABSTRACT

A new and distinct cultivar of geranium with yellow-green foliage and large singe violet-blue blossoms, these blossoms starting from mid June and continuing through to early October. This geranium forms spreading mounded clumps, and is ideal for use in borders or containers that do not become too dry.

2 Drawing Sheets

The present invention relates to a new and distinct variety of hardy perennial herbaceous plant of the genus Geranium a member of the Geraniaceae family and hereinafter referred to by the cultivar name 'BLOGOLD'.

This new cultivar of Geranium arose as a chance seedling at the nursery of

Mr Hans Kramer
Kwerkerij de Hessenhof
Hessenweg 41
6718 TC Ede
Netherlands.

The true parentage of Geranium 'BLOGOLD' is not known.

Geranium 'BLOGOLD' was discovered in August of 1994. Geranium 'BLOGOLD' is the result of this single seedling being grown and observed and the unique characteristics of which include yellow-green foliage with almost orange stems in the spring and yellow green foliage at flowering, the flowers being, violet-blue, distinguish Geranium 'BLOGOLD' as a new and distinct cultivar.

The new cultivar has been reproduced from this single plant asexually by division and basal cuttings. This asexual reproduction has shown the unique features of the new cultivar to be stable and that they are reproduced true to type in successive generations. The first asexual reproduction of the cultivar was carried out by Hans Kramer at his aforementioned nursey.

Geranium 'BLOGOLD' forms spreading mounded clumps with deeply cut divided yellow-green leaves, Geranium 'BLOGOLD'will flower for many weeks starting mid June through to early October. Geranium 'BLOGOLD' can be compared to Geranium 'ANN FOLKARD' (not patented).

Geranium 'BLOGOLD' differs from Geranium 'ANN FOLKARD' by way of the combination of foliar and flower color. A detailed comparison of plants of the cultivars 'BLOGOLD' and 'ANN FOLKARD' appears in chart A.

The plant thrives best in full sun and well drained soil. The plant does not succeed well in dry shade. The plants were observed at the nursery of Blooms of Bressingham, Ltd. in Bressingham, Diss, Norfolk, England, under normal UK conditions, throughout the growing season, February until November.

BRIEF DESCRIPTION OF THE DRAWINGS

The accompanying drawings illustrate the overall appearance of the new Geranium showing colors as true as it is reasonably possible to obtain in colored reproductions.

The first drawing shows the flower and foliage colors.

The second drawing is a top view of 'BLOGOLD' in the spring.

CHART A

| CHARACTERISTIC | Geranium 'BLOGOLD' | Geranium 'ANN FOLKARD' |
|---|---|---|
| STEM COLOR | Yellow-Green RHS 145 B Becoming Red RHS 41 A | Green RHS 139 B becoming Greyed-Red RHS 179 B |
| LEAF LENGTH | 8 cm | 10 cm |
| LEAF WIDTH | 10 cm | 12 cm |
| LEAF COLOR UPPER SURFACE | Young-Orange-Red RHS 30 C Mature-Green-Yellow RHS 1 A | Young-Yellow-Green RHS 145 A Mature-Yellow-Green RHS 145 B |
| LEAF COLOR LOWER SURFACE | Young Yellow-Orange RHS 23 C Mature-Yellow-Green RHS 145 C | Young-Yellow-Green RHS 144 C Mature-Yellow-Green RHS 144 C |
| PETIOLE LENGTH | 10 cm | 15 cm |
| PETIOLE COLOR | Yellow-Green RHS 145 B becoming Red RHS 41 A | Green RHS 139 B becoming greyed-red RHS 179 B |
| FLOWERING PERIOD | Mid June to Early Oct/16 weeks | Mid June to Mid Sept./12 weeks |

CHART A-continued

| CHARACTERISTIC | Geranium 'BLOGOLD' | Geranium 'ANN FOLKARD' |
|---|---|---|
| FRAGRANCE | None | None |
| FLOWER LENGTH | — | — |
| FLOWER DIAMETER | 4 cm | 3 cm |
| SEPAL COLOR UPPER SURFACE | Yellow-Green RHS 145 C | Green RHS 139 D |
| SEPAL COLOR LOWER SURFACE | Yellow-Green RHS 145 C | Green RHS 139 D |
| PEDUNCLE STEM COLOR | Yellow-Green RHS 145 A becoming Red RHS 41 A | Green RHS 139 B becoming greyed-red 179 B |

DETAILED BOTANICAL DESCRIPTION

The following is a detailed description of the new Geranium variety. All color determinations and comparisons are based on The Royal Horticultural Society Colour Chart.

Orgin: Seedling discovered in a cultivated setting.
Parentage: Unknown.
Habit: Spreading mounded clumps.
Size: Mature plants are 40 cm in height with a spread of 60 cm.
Root system: Fleshy and fibrous.
Plant vigor: A perennial that shows vigorous and healthy growth throughout Great Britain.
Blooming habit: Showy single violet blue flowers. The flowers are clearly veined. More than 35 blooms per plant. Blooms will last approximately 7 to 10 days. Flowering habit is continuous from June to October. The flowers are single and arranged in umbels.
Blooming period: From mid-June continuing into early October. Geranium 'BLOGOLD'was grown and observed at Blooms of Bressingham, Ltd. of Bressingham, Diss, Norfolk, England.
Hardiness: Winter hardy throughout the Bristish Isles. The plant has not been fully tested for maximum summer tolerance above 32° C. (90° F.).
Branching habit: Leaves and flower stems arise from the central crown rootstock. Leaves will arise on a single petiole, which will range from 5 cm in the spring to 40 cm for a mature plant. Flower peduncles will arise from the central crown root stock, and will branch 4 to 8 times. Branch length will be up to 40 cm; internode length is 12 cm.
Disease resistance: None particulary shown, no more susceptibility to pest and disease problems than other Geraniums.
Stem: Color: RHS orange-red 34A.

FOLIAGE

Arrangement: Leaves in pairs, 5 to 7 deeply cut divisions. The leaf pairs are opposite.
Type: Herbaceous perennial.
Texture: Both upper and lower surfaces moderately hairy.
Length: 8 cm.
Width: 10 cm.
Leaf shape: Palmate, deeply lobed and pointed.
Petiole length: 10 cm.
Petiole color: Yellow-green RHS 145 B becoming red RHS 41 A towards leaf and later in growing season.
Stipules: Present, 12 mm.
Margins: Incised.
Apices: Acute.
Base: Sagitate.
Venation: Pinnate.
Upper leaf venation color: RHS orange-red 41 A in spring, to RHS yellow-green 145A during summer.
Lower leaf venation color: RHS orange-red 41 B in spring, to RHS yellow-green 145 C during summer.
Lobing: Deeply parted.

FLOWERS

Petal: 5 of similar size. Petals are clearly veined.
Petal size: 5 petals, 2 cm long by 1.5 cm wide at the outer edge, down to 2 mm at the base of the petal.
Petal shape: Orbicular.
Bud size: 1 cm.
Bud shape: Boat-shaped with a ridge running down the center.
Bud color: Vein color is RHS yellow-green 144 B; bud is RHS yellow-green 145 B becoming RHS red 41 B near the edges.
Arrangement: In umbels, single, stalked.
Pubescence: Present on the base edge petal extending up approximately 0.5 cm.
Flower shape: Saucer shaped.
Flower size: 4 cm diameter.
Sepal texture: Carinate and soft.
Sepal arrangement: 5, persistent, imbricate.
Sepal strength: Firm.
Sepal size: 5.
Sepal shape: Arranged star-like, margin tips are entirely pungent.
Sepal margin: Entire.
Sepal tip: Pungent.
Sepal color: Yellow-green RHS 145 C.
Peduncle: Strong.
Peduncle color: Yellow-green RHS 145 A becoming red RHS 41 A towards flower.
Peduncle texture: Stiff.
Peduncle length: Up to 40 cm.
Peduncle diameter: Up to 2 mm.
Pedicel texture: Stiff.
Pedicel length: 2 to 3 cm.
Pedicel diameter: 1 mm.
Pedicel color: RHS orange-red 34A.

REPRODUCTIVE ORGANS

Stamens: 10.
Anthers: 0 to 10, sometimes absent, purple RHS 79 A.
Pollen: Little pollen is produced, yellow-green RHS 154 D.
Stigma/style: Purple RHS 79 C.
Ovary: Yellow-green RHS 150D.
Filament color: RHS purple 79C.
Pistils: 5.
Seed development: Only a small amount of seed is produced.
Seed colour: Greyed-orange RHS 177A.
Seed dispersal: The mericarp with the seed inside and the awn attached comes away from the central column, being thrown a short distance. After discharge the central column is empty.

COLOUR CHARACTERISTICS

FOLIAGE

Young leaves:
*Upper surface.*—Orange-red RHS 30C.
*Under surface.*—Yellow-orange RHS 23C.
Mature leaves:
*Upper surface.*—Green-yellow RHS 1A.
*Under surface.*—Yellow-green RHS 145C.
*Leaf margins.*—Tint of orange-red RHS 30 C.
Petals when opening:
*Upper side.*—Violet-blue RHS 89C.
*Under side.*—Violet-blue RHS 90C.
Petals when fully open: These are veined.
*Upper side.*—Violet-blue RHS 96C.
*Veins.*—Violet RHS 87A.
*Under side.*—Violet-blue RHS 89C.
*Veins.*—Violet RHS 87B.

I claim:

1. A new and distinct cultivar of geranium, substantially as shown and described herein, characterized by its combination of yellow green foliage and many large single violet-blue blossoms arranged as compound dichasial Cymes.

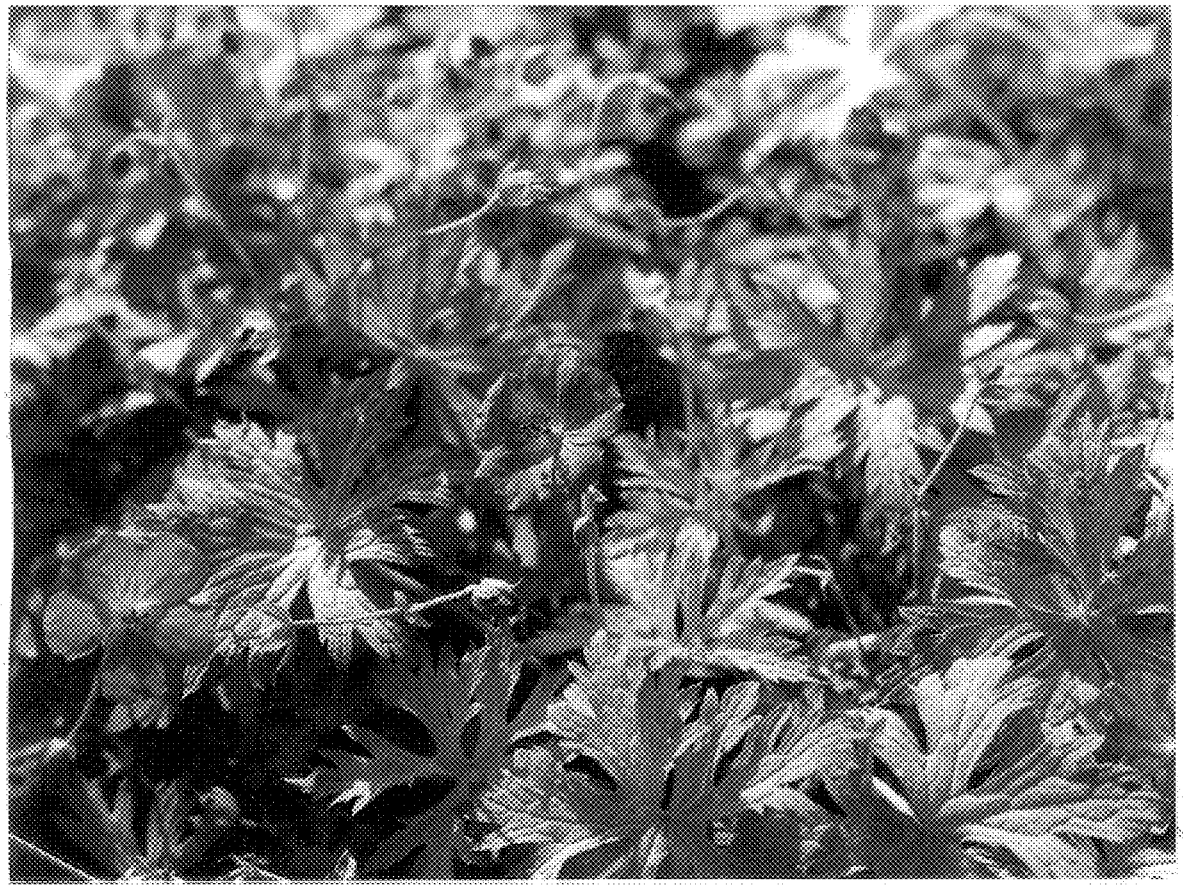

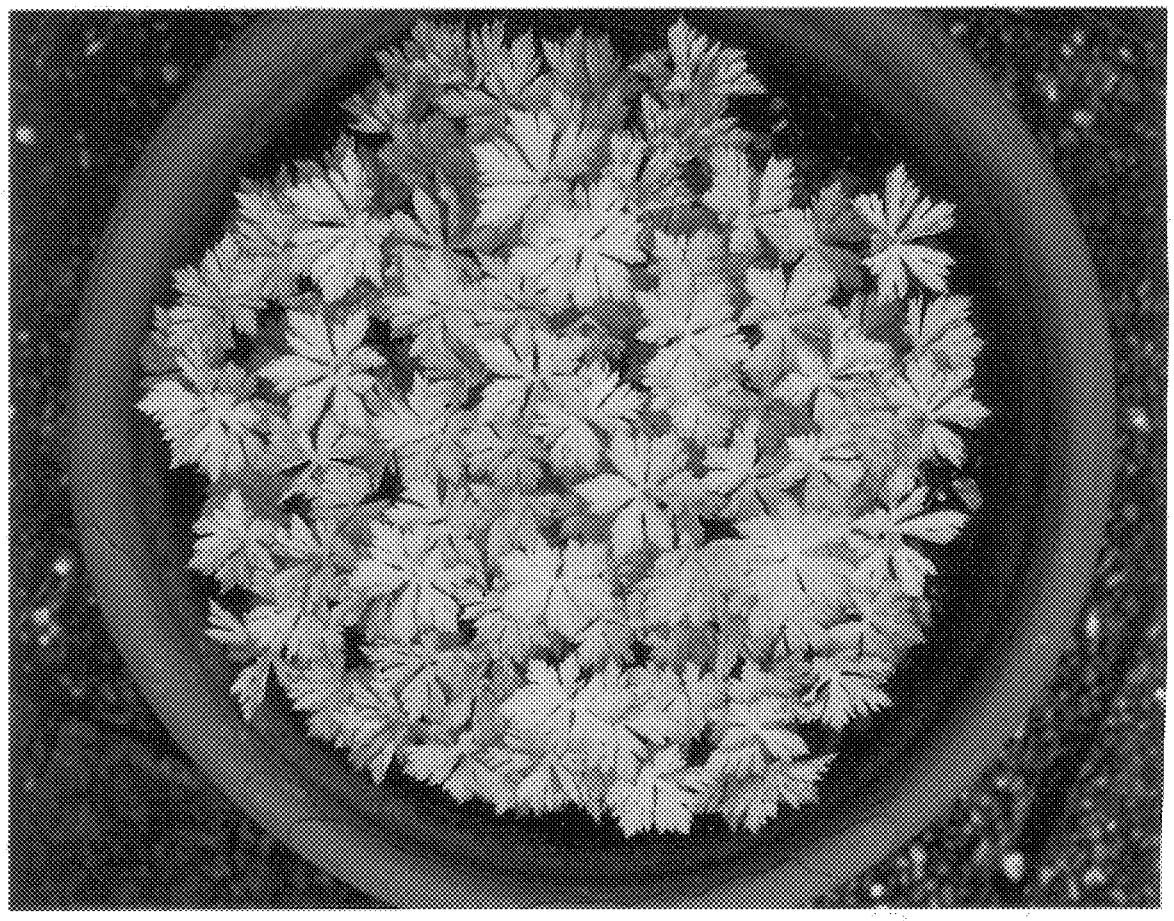

* * * * *